United States Patent
Dubov

(10) Patent No.: US 8,367,795 B2
(45) Date of Patent: Feb. 5, 2013

(54) ANTISEPTIC MATERIAL AND A METHOD FOR THE PRODUCTION AND USE THEREOF

(75) Inventor: Oleg Vladimirovich Dubov, Saint-Petersburg (RU)

(73) Assignee: OOO Aquaphor, Saint-Petersburg (RU)

( * ) Notice: Subject to any disclaimer, the term of this patent is extended or adjusted under 35 U.S.C. 154(b) by 277 days.

(21) Appl. No.: 12/739,690

(22) PCT Filed: Sep. 3, 2008

(86) PCT No.: PCT/RU2008/000583
§ 371 (c)(1),
(2), (4) Date: Apr. 23, 2010

(87) PCT Pub. No.: WO2009/054748
PCT Pub. Date: Apr. 30, 2009

(65) Prior Publication Data
US 2010/0249334 A1    Sep. 30, 2010

(30) Foreign Application Priority Data

Oct. 24, 2007  (RU) ................................ 2007139459

(51) Int. Cl.
*C08G 12/32* (2006.01)
*C08G 14/10* (2006.01)
*C08G 12/02* (2006.01)
*C08G 12/40* (2006.01)

(52) U.S. Cl. .......................... 528/242; 528/243; 528/257
(58) Field of Classification Search .................. 525/326; 528/242, 243, 257
See application file for complete search history.

(56) References Cited

U.S. PATENT DOCUMENTS

| 3,948,853 A | 4/1976 | Horning et al. |
| 4,594,392 A | 6/1986 | Hatch |
| 5,490,983 A | 2/1996 | Worley et al. |

FOREIGN PATENT DOCUMENTS

| CA | 849614 | 8/1970 |
| CA | 965699 | 4/1975 |
| CA | 995841 | 8/1976 |
| RU | 2167707 | 5/2001 |
| WO | WO 81/00340 | 2/1981 |

*Primary Examiner* — Duc Truong
(74) *Attorney, Agent, or Firm* — Arent Fox LLP; Michael Fainberg

(57) ABSTRACT

The invention relates to chemical industry, in particular to a substance with antiseptic properties and to a method for obtaining and use thereof. The inventive substance can be used as a filtering material or an additive for the mixture of filtering materials, or as a component of filtering composites used for disinfection and purification of liquids, preferably drinking water, or gases. The inventive antiseptic material consists of a solid non-water soluble cross-linked polymer material, which comprises chlorine atoms reversibly bound with nitrogen atoms and is characterized by the following general formula: $M(F)1.0-5.5(Ph)0.6-1.0Cl-4.2$, where M is melamine, F—bridge and terminal groups—formaldehyde derivatives, Ph—phosphorus with oxidation level +5, Cl—chlorine atoms bound with nitrogen atoms, wherein the above-mentioned material is cross-linked by binding phosphorus-containing ions with melamine links of polymer chains.

17 Claims, No Drawings

ANTISEPTIC MATERIAL AND A METHOD FOR THE PRODUCTION AND USE THEREOF

CROSS-REFERENCE TO RELATED APPLICATION

This application is a National Stage entry of International Application No. PCT/RU2008/000583, filed Sep. 3, 2008 which claims the benefit of priority from Russian Application No. 2007/39459 filed Oct. 24, 2007. The disclosures of the prior applications are hereby incorporated herein in its entirety by reference.

FIELD OF INVENTION

The invention relates to chemical industry and in particular to a substance having antiseptic properties, as well as to a method for production and use thereof. The invention may be used as a filtering material or an additive to the mixture of filtering materials or a component of filtering composite materials for disinfection and purification of liquids, preferably drinking water, or gases.

BACKGROUND

From the U.S. Pat. No. 4,594,392, there is known a stable combined form of halogenated and/or interhalogenated resins for disinfection of water, comprising a copolymer in the form A/B-X, wherein X includes polyvinylpyridine, having functional pyridyl group $C_5H_5N$, being cross-linked with approximately 2-25% of divinylbenzene, wherein A/B is a combination of halogens and/or interhalogens, attached to the nitrogen atom of the functional pyridil group X. The process of obtaining such material comprises processing with halogenides and/or interhalogenides solution in methanol, methyl chloride or chloroform and further washing of the obtained material with water.

Use of poisonous and expensive components in the process of production of the said polymer material not only complicates the process itself but also increases the net cost of the final product, while the obtained polymer material for water disinfection evolves into this water iodine and bromine which are extremely poisonous. Iodine excess leads to thyroid gland diseases while that of bromine leads to the nervous system diseases.

The closest analogue (prototype) of the present invention is a solid water-insoluble cross-linked polymer material selected from the group comprising urea-formaldehyde, melamine-formaldehyde, urea-melamine-formaldehyde resins, described in the Canadian Patent No. 849 614, comprising chlorine atoms reversibly bound with nitrogen atoms and containing no less than 1% of chlorine by weight.

The described polymer material contains weak bonds between nitrogen and chlorine atoms and easily yields chlorine into the environment, thus it can be used for disinfection of different sources of water. This material is obtained by passing at room temperature of gaseous chlorine through aqueous suspension of cross-linked polymer resin, selected from the group comprising urea-formaldehyde, melamine-formaldehyde, urea-melamine-formaldehyde resins.

A disadvantage of such material is that it cannot retain chlorine. In storage, such material self-oxidizes and deteriorates. The process of producing such material needs additional components and stages during chlorination, which complicates the method of production, increases power consumption and eventually increases the net costs of the product. In order to make the product water-insoluble, there is a need for a cross-linkage stage, which, in case melamine-formaldehyde resin is used, takes place in the presence of the additional component such as monohydrate glyoxal, which is poisonous. The process of producing urea-melamine-formaldehyde resin is multistage, needs additional ingredients and is time-consuming. Cross-linkage of urea-formaldehyde resin takes a long time, about 17 hours. Such use of above-described resins for producing chlorinated polymer material is associated with a complicated and time-consuming process of the producing the resin itself, which leads to increased power consumption while usage of free chlorine atom at the stage of chlorination reduces ecological compatibility.

A further development of the invention described in the Canadian Patent No. 849 614 is a solid water-insoluble cross-linked polymer material described in the U.S. Pat. No. 3,948,853, which comprises chlorine atoms reversibly bound with nitrogen atoms, the content of nitrogen being no less than 1% by weight, selected from the group, comprising a) urea-formaldehyde resin; b) melamine-formaldehyde resin; c) urea-melamine-formaldehyde resin; wherein in each case the resin is stabilized by chlorine dioxide or hypochlorite or by multiple chlorination. The inventors proposed a method for stabilization of polymer material to enhance of its resistance to self-oxidation. However, such method of producing a stabilized resin is even more complicated as compared to its prototype, as it comprises additional stages, namely exposure to hypochlorites and chlorine dioxide. Eventually these lead to greater power consumption and an increase in the net costs of the final product, while its resistance to self-oxidation does not improve significantly, approximately up to 3 months, which is not suitable for a long-term storage and long-distance shipment.

There are known polymer cyclic biocidal compounds, comprising N-galamines (galamines meaning chlorine and bromine amines) described in the U.S. Pat. No. 5,490,983. The inventors propose polymer cyclic biocidal compounds and methods of use thereof, wherein functional groups in such compounds, such as halogenated hydantoins, triazine diones or pyrimidinones are mixed with cheap polymer links such as polystyrene, polyethylene or modified polymethacrylamide ones. Said polymer compounds are stable and recyclable insoluble biocides, which yield only small amounts of free halogen and admixtures into the water. They can be used as disinfectants for drinking water, swimming pools, hot baths, industrial water supply systems, heating columns, air conditioning systems, gas flows, paints, oils, ointments, tissues, sterile dressings, coatings, solid surfaces, inserts and containers etc.

Among their disadvantages there are high net costs and low ecological compatibility of the production process itself. Moreover, this process is complicated and is highly work- and power consuming, as expensive and poisonous components are used, namely acetylchloride and carbon disulphide, their vapors being dangerously explosive when contacting with air. Use of compounds that are dangerous for humans exerts an adverse effect on the environment at the place of production and in its vicinity.

SUMMARY

The objective resolved by the authors of the present invention consists in providing a stable antiseptic material capable of multiple regeneration, produced using a simple method and having low net costs, which can be used as a filtering material or an additive for the mixture of filtering materials, or as a component of filtering composites used for purification and disinfection of liquids, preferably drinking water, or gases.

The technical effect of the present invention consists in the implementation of intended use of the proposed antiseptic material, reduced economical and power demands of its production, as well as in improved ecologic compatibility and simplification of the process of its production.

The technical effect is achieved by the following:

An antiseptic material, which consists of a solid non-water soluble cross-linked polymer material, containing chlorine atoms reversibly bound with nitrogen atoms, according to the present invention has a general formula: $M(F)1.0-5.5(Ph)0.6-1.0Cl-4.2$, where M is melamine, F—bridge and terminal groups—formaldehyde derivatives, Ph—phosphorus with oxidation level +5, Cl—chlorine atoms bound with nitrogen atoms, wherein the above-mentioned material is cross-linked by binding phosphorus-containing ions with melamine links of polymer chains, wherein said polymer material is a powder or granules or a mixture thereof, wherein granules are a porous material 0.1-4 mm in size, preferably 0.3-2 mm, which is resistant to self-oxidation, is capable of inactivation of microorganisms at immediate contact in liquid and gaseous environments, yields active chlorine into the liquid environment in the controlled concentration no less than 0.01 mg/l but no more than 4 mg/l, preferably 0.1-1.5 mg/l, more preferably 0.2-0.4 mg/l, which does not significantly depend on pH level or temperature of the environment, being safe for humans and sufficient for a long-term maintenance of the antiseptic effect of the environment; oxidizes reductants, e.g. arsenite, hydrogen sulfide, ferrous iron. A method of producing the inventive antiseptic material includes chlorinating solid non-water soluble cross-linked polymer material and uses a product, which is produced by condensation of melamine phosphate and paraform or soluble non-organic phosphate, melamine and paraform in an aqueous solution, wherein the above-mentioned material is cross-linked by binding the phosphorus-containing ions with melamine links of polymer chains immediately in the process of obtaining said product, whereas an aqueous solution of hypochlorites of alkaline metals is used as a chlorinating agent, e.g. those of sodium, potassium, lithium or alkali-earth metals, for example that of calcium. Use of the antiseptic material, consisting of a solid water-insoluble cross-linked polymer material, which comprises chlorine atoms reversibly bound with nitrogen atoms and has the following general formula: $M(F)1.0-5.5(Ph)0.6-1.0Cl-4.2$, where M is melamine, F—bridge and terminal groups—formaldehyde derivatives, Ph—phosphorus with oxidation level +5, Cl—chlorine atoms bound with nitrogen atoms, wherein the above-mentioned material is cross-linked by binding phosphorus-containing ions with melamine links of polymer chains as a filtering material, as an additive to the mixture of filtering materials or component of the filtering composites for disinfection and purification of liquids or gases.

The antiseptic material is obtained as follows:

A mixture of melamine phosphate, water and paraform or soluble non-organic phosphate, melamine, water and paraform is heated while being stirred. Consequently, depending on the conditions of stirring, a product is obtained in the form of powder or granules or mixture thereof, wherein granules are of a porous material, in particular a hydrophilic one, 0.1-4 mm in size, preferably 0.3-2 mm. Then the reaction liquid is removed, the product is washed with water and treated at the room temperature with a water solution of hypochlorites of alkaline metals, for example those of sodium, potassium, lithium, or alkali-earth metals, for example that of calcium. The obtained material disinfects liquid being run through it, annihilates bacteria and viruses and may be used as a filtering material for purification of liquids, for example drinking water, swimming pool water, waste water, process liquids; it may be also used as a component of filtering composites. It can be deposited on fibers, films, granules and other solid carriers; this can be done immediately during the process of polymerization in order to achieve a synergetic effect or for more convenient usage.

The antiseptic material is characterized as follows:

due to the balanced hydrolysis, it yields active chlorine into the running water in a controllable concentration of no less than 0.01 mg/l, but no more than 4 mg/l, preferably 0.1-1.5 mg/l, more preferably 0.2-0.4 mg/l. A low concentration of the yielded active chlorine is safe for human health, maintains the biocidal properties of the disinfected liquid in further storage and prevents the formation of chlorinated organic compounds which easily emerge in case of water chlorination with gaseous chlorine and are poisonous;

it oxidizes reductants, namely arsenites, hydrogen sulfide, ferrous iron salts, transforming them into harmless substances;

is highly resistant to self-oxidation;

is capable of effective inactivation of microorganisms at immediate contact in a liquid or gaseous environment;

concentration of active chlorine yielded into the liquid environment by said material does not significantly depend on pH level and temperature of the environment.

As compared to the prototype, no additional steps of cross-linking or usage of any toxic linking agent are necessary for obtaining the material according to the present invention. Cross-linking is achieved by binding phosphorus-containing ions with melamine links of polymer chains immediately in the process of producing the polymer material. Usage of hypochlorites in the production of the antiseptic material improves the ecological compatibility of the production method. Fast saturation with active chlorine approximately up to 90-95% during the first hour of chlorination according to the proposed method of production of the antiseptic material reduces power consumption and increases the efficiency of said method.

Regeneration of the antiseptic material after depletion may be performed by passing a water solution of hypochlorites of alkaline metals or alkali-earth metals through the material, wherein such regeneration may be performed in the running mode.

DETAILED DESCRIPTION

EXAMPLES OF OBTAINING THE ANTISEPTIC MATERIAL:

Example 1

22.7 grams (g) of melamine phosphate, 7.5 g of paraform and 4 g of NaOH were put into a round-bottom flask (200 ml) with a mechanical stirrer, then 100 ml of water were added. The mixture was actively stirred (1200 rpm) at 90° C. for 4 hours. The obtained product had the form of porous granules 0.3-2 mm in size. The mass of the obtained product was 29.8 g, mole ratio of the melamine derivatives/phosphorus/formaldehyde derivatives was 110/92/2.47. Mole fraction of the terminal methylol groups in formaldehyde derivatives was 0.013 (according to infrared spectroscopy data).

The granules were washed using a Buchner funnel.

The obtained polymer was chlorinated while stirring for 1 hour with 300 ml of sodium hypochloride with active chlorine concentration of 52 g/l.

The chlorinated product was washed with water using a Buchner funnel up to neutral reaction, and then was dried at 50° C.

The product comprised 29% of active chlorine (the chlorine content was assessed iodometrically).

Example 2

12.6 g of melamine, 7.5 g of paraform and 21.0 g of sodium dihydrogen phosphate dihydrate were put into a round-bottom flask (200 ml) with a mechanical stirrer, then 100 ml of water were added. The mixture was actively stirred (1200 rpm) at 90° C. for 4 hours. The obtained product was porous, in the form of granules 0.3-2 mm in size. The mass of the obtained product was 29.2 g.

Mole ratio of the components is the same as in Example 1.

The granules were washed with water using a Buchner funnel.

The obtained polymer was chlorinated while stirring for 1 hour with 300 ml of sodium hypochloride with active chlorine concentration of 52 μl.

The chlorinated product was washed with water using a Buchner funnel up to neutral reaction, and then was dried at 50° C.

The product comprised 28% of active chlorine (the chlorine content was assessed iodimetrically).

Example 3

The polymer material was obtained by the method described in Example 1.

The obtained product was chlorinated while being mixed with an aqueous suspension of chloride lime (80 g of CaCl(OCl)) and retained for 5 hours.

The chlorinated product was washed with acid (100 ml of 10% solution) and water using a Buchner funnel, then dried at 50° C.

There was obtained a product containing 26% of active chlorine.

Examples Confirming the Properties and Implementation of the Intended Use of the Antiseptic Material Example 4

Through the funnel 2 cm in diameter and 10 cm in length, containing 50 g of the product obtained in Examples 1-3 (hereinafter referred to as "the funnel") distilled water was poured with different initial pH levels at a rate of 0.1 l/minute at 25° C.

pH level of the poured water was set by adding sodium hydroxide or hydrochloric acid.

In the outgoing water, active chlorine concentration was iodometrically estimated (titration with sodium thiosulfate). The following correlation of the chlorine concentration with poured water volume was registered:

| Poured volume, l | Concentration of active chlorine, mg/l | | |
|---|---|---|---|
| | pH = 4 | pH = 7.5 | pH = 10 |
| 10 | 0.370 | 0.362 | 0.384 |
| 100 | 0.310 | 0.303 | 0.326 |
| 150 | 0.302 | 0.297 | 0.316 |
| 200 | 0.290 | 0.282 | 0.301 |
| 250 | 0.276 | 0.266 | 0.285 |
| 300 | 0.258 | 0.251 | 0.271 |
| 350 | 0.225 | 0.220 | 0.253 |
| 400 | 0.210 | 0.204 | 0.238 |

Example 5

Distilled water with initial pH level 7.5 was poured through the funnel at a rate of 0.1 l/minute at 5° C. and 45° C. The following correlation of the chlorine concentration with poured water volume was registered:

| Poured volume, l | Concentration of active chlorine, mg/l | |
|---|---|---|
| | T = 5° C. | T = 45° C. |
| 10 | 0.360 | 0.340 |
| 100 | 0.300 | 0.289 |
| 150 | 0.289 | 0.277 |
| 200 | 0.273 | 0.260 |
| 250 | 0.260 | 0.254 |
| 300 | 0.248 | 0.242 |
| 350 | 0.215 | 0.210 |
| 400 | 0.201 | 0.206 |

Example 6

A suspension of *E. Coli* bacteria in concentration of 10000 cells/ml was poured through the funnel at a rate of 0.1 l/min at 25° C. Output bacteria concentration was estimated in every 20 liters using the method of plating with peptone agar. Output concentration of the bacterial cells was as follows:

| Poured volume, l | Concentration of cells (CFU), average of 3 platings, CFU/ml |
|---|---|
| 10 | 0 |
| 100 | 0 |
| 150 | 0 |
| 180 | 15 |
| 200 | 120 |
| 220 | 306 |
| 300 | 2045 |

Thus, for this mode of pouring the resource for *E. Coli* was 3200 l of water per 1 kg of the product.

Example 7

A suspension of *Bacillus subtilis* cells was poured through the funnel in the same conditions as in Example 6. Output concentration of the bacterial cells was as follows:

| Poured volume, l | Concentration of cells (CFU), average of 3 platings, CFU/ml |
|---|---|
| 10 | 0 |
| 100 | 0 |
| 200 | 0 |
| 220 | 0 |
| 240 | 6 |
| 260 | 87 |
| 280 | 403 |
| 400 | 1608 |

Thus, for this mode of pouring the resource for *Bacillus subtilis* was 4400 l of water per 1 kg of the product.

Example 8

A suspension of viruses (bacteriophages) MS-2 with a concentration of viral particles being $10^5$/ml was poured through the funnel in the same conditions as in Example 6. Output concentration of the viral particles was as follows:

| Poured volume, l | Concentration of cells (CFU), average of the 3 platings, CFU/ml |
|---|---|
| 10 | 0 |
| 50 | 0 |
| 70 | 0 |
| 100 | 23 |
| 200 | 107 |
| 300 | 313 |
| 400 | 502 |

Thus, for this mode of pouring the resource for MS-2 was 1400 l of water per 1 kg of the product.

Examples 6, 7 and 8 confirm the antibacterial and antiviral activity of the proposed material.

Example 9

100 ml of *E. Coli* suspension with concentration of 1000 cells/ml were stirred for one hour using a magnetic stirrer with 2 g of the substance obtained in Example 1.

In the control experiment 2 g of the product were stirred for one hour with 100 ml of distilled water, then water was separated by filtration with a paper filter. The concentration of the active chlorine in this water was 384 µl. Further, 1 ml of *E. Coli* suspension with concentration of $10^5$ cells/ml was added into this water, then the mixture was stirred for one hour.

The solution obtained in the first experiment turned out to be sterile. The concentration of the live cells in the second solution was 72 CFU/ml (average of the three iterations).

Thus, the antibacterial activity of the proposed material is significantly higher than that of the active chlorine being balanced with it.

Example 9 confirms the capability of the proposed antiseptic material to inactivate microorganisms on immediate contact.

Example 10

In the same conditions as in Example 6, a Mohr's salt solution with $Fe^{2+}$ concentration of 50 mg/l was poured through the funnel. A decrease in the output concentration of ferrous iron was registered (due to its oxidation into the ferric iron).

| Poured volume, l | Concentration of $Fe^{2+}$, mg/l |
|---|---|
| 50 | 0.1 |
| 200 | 0.3 |
| 400 | 0.6 |
| 600 | 1.5 |
| 800 | 2.3 |
| 1000 | 4.1 |

Example 11

In the same conditions as in Example 6, a Mohr's salt solution with $As^{3+}$ in concentration of 10 mg/l was poured through the funnel. A decrease in the output concentration of trivalent arsenic was registered (due to its oxidation into pentavalent arsenic).

| Poured volume, l | Concentration of $As^{3+}$, mg/l |
|---|---|
| 50 | 0.02 |
| 200 | 0.09 |
| 400 | 0.13 |
| 600 | 0.52 |
| 800 | 1.4 |

Example 12

In the same conditions as in Example 6, hydrogen sulfide solution with $S^{2-}$ concentration of 10 mg/l was poured through the funnel. A decrease in the output concentration of bivalent sulfur and its conversion into sulfate-ions was registered.

| Poured volume, l | Concentration of $S^{2-}$, mg/l |
|---|---|
| 10 | 0.15 |
| 20 | 0.3 |
| 50 | 0.55 |
| 70 | 1.4 |
| 100 | 2.2 |

Examples 10, 11, 12 confirm the capability of the proposed antiseptic substance to oxidize reductants, converting them into safe substances.

Example 13

Experimental studies of the antiseptic material resistance to self-oxidation were carried out. The chlorine content in the product in the initial concentration of 20% by weight decreases to 19.2% by weight when the product is stored for 8 moths at a room temperature away from moisture, and to 17% when the product is stored for 8 months at a room temperature under water.

In spite of the fact that the present invention was described in connection to the embodiments being the most advantageous and preferred, it should be understood that the present invention is not limited by the described embodiments, on the contrary, it encompasses different modifications and embodiments that are within the spirit and scope of the following claims.

The invention claimed is:

1. An antiseptic material, consisting of a solid water-insoluble cross-linked polymer material, which comprises chlorine atoms reversibly bound with nitrogen atoms, characterized in that the material is a polymer material of the following general formula:

$$M(F)_{1.0-5.5}(Ph)_{0.6-1.0}Cl_{-4.2}$$

where M is melamine, F are bridge and terminal groups—formaldehyde derivatives, Ph is phosphorus with oxidation level +5, Cl is chlorine atoms bound with nitrogen atoms, wherein said polymer material is cross-linked by binding phosphorus-containing ions with melamine links of polymer chains.

2. The antiseptic material of claim 1, characterized in that the antiseptic material yields active chlorine into the liquid environment in a controllable concentration, which does not significantly depend on pH level or temperature of the environment, is safe for humans and sufficient for maintaining a biocidal effect of the environment during a long term.

3. The antiseptic material of claim 2, characterized in that the antiseptic material yields active chlorine in the concentration no less than 0.01 mg/l but not more than 4 mg/l.

4. The antiseptic material of claim 1, characterized in that the antiseptic material is resistant to self-oxidation.

5. The antiseptic material of claim 1, characterized in that the antiseptic material is capable of inactivating microorganisms at immediate contact in liquid and gaseous environments.

6. The antiseptic material of claim 1, characterized in that the antiseptic material oxidizes reductants, for example arsenites, hydrogen sulfide, ferrous iron.

7. The antiseptic material of claim 1, characterized in that the antiseptic material is in the form of a powder.

8. The antiseptic material of claim 1, characterized in that the antiseptic material is in the form of granules.

9. The antiseptic material of claim 1, characterized in that the antiseptic material is in the form of a mixture of powder and granules.

10. The antiseptic material of claim 8, characterized in that the size of the granules is 0.1-4 mm.

11. The antiseptic material of claim 8, characterized in that the granules are porous.

12. The antiseptic material of claim 9, characterized in that the size of the granules is 0.1-4 mm.

13. The antiseptic material of claim 9, characterized in that the granules are porous.

14. The antiseptic material of claim 3 characterized in that the antiseptic material yields active chlorine in the concentration no less than 0.1 mg/l but not more than 1.5 mg/l.

15. The antiseptic material of claim 14 characterized in that the antiseptic material yields active chlorine in the concentration no less than 0.2 mg/l but not more than 0.4 mg/l.

16. The antiseptic material of claim 10, characterized in that the size of the granules 0.3-2 mm.

17. The antiseptic material of claim 12, characterized in that the size of the granules is 0.3-2 mm.

* * * * *